United States Patent [19]
Bhutani

[11] 3,935,264
[45] Jan. 27, 1976

[54] HYDROGENATION OF DINITROTOLUENE TO TOLUENE DIAMINE

[75] Inventor: Sudhir K. Bhutani, West Haven, Conn.

[73] Assignee: Olin Corporation, New Haven, Conn.

[22] Filed: June 19, 1974

[21] Appl. No.: 480,796

[52] U.S. Cl. .............................................. 260/580
[51] Int. Cl.² ......................................... C07C 85/10
[58] Field of Search .................................... 260/580

[56] References Cited
UNITED STATES PATENTS

| | | | |
|---|---|---|---|
| 3,517,063 | 6/1970 | Nason | 260/580 |
| 3,637,820 | 1/1972 | Dodman et al. | 260/580 X |
| 3,666,813 | 5/1972 | Hindlin et al. | 260/580 |
| 3,678,108 | 7/1972 | Arrigo | 260/580 X |
| 3,801,640 | 4/1974 | Knifton | 260/580 X |

*Primary Examiner*—Paul F. Shaver
*Attorney, Agent, or Firm*—F. A. Iskander; T. P. O'Day

[57] ABSTRACT

An improved process is disclosed for the hydrogenation of dinitrotoluene to toluene diamine in the presence of an aliphatic alcohol solvent. Aimed at preventing the formation of N-alkyl toluene diamine by-product, the improvement resides in carrying out the hydrogenation reaction in the presence of a small proportion of carbon monoxide.

13 Claims, No Drawings

HYDROGENATION OF DINITROTOLUENE TO TOLUENE DIAMINE

This invention relates to a select improvement in the hydrogenation of dinitrotoluene to the corresponding toluene diamine.

Toluene diamine is a valuable chemical that has been used extensively as an intermediate in the preparation of toluene diisocyanate. The latter in turn is a universally known and widely used intermediate in the production of polyurethane elastomers and foams.

Numerous methods have been disclosed in the patent literature for the reduction of dinitrotoluene to toluene diamine using hydrogen or carbon monoxide. See for example U.S. Pat. No. 2,894,036, No. 3,328,465, No. 3,356,728, No. 3,517,063 and No. 3,637,820. One of the commercially popular processes for carrying out this reduction reaction calls for the hydrogenation of dinitrotoluene in the presence of an aliphatic alcohol solvent, such as methanol, and a metallic catalyst such as Raney nickel. This process has been widely used in industry inasmuch as it represents an economically feasible route to the production of toluene diamine in high yields.

However, it has been found that the hydrogenation of dinitrotoluene in the presence of an aliphatic alcohol solvent has one drawback. This is that it often results in the formation of a relatively small proportion of an undesirable by-product, namely, N-alkyl toluene diamine. The formation of this by-product, which results from the presence of the aliphatic or alkyl alcohol in the reaction mixture, is undesirable for two reasons. One is that its formation in effect represents a reduction in the net yield or output of toluene diamine. Secondly, and more importantly, this by-product constitutes a highly objectionable impurity when the toluene diamine is subsequently reacted with phosgene to produce toluene diisocyanate. In this reaction, the N-alkyl toluene diamine is converted to carbamyl chloride which is easily hydrolyzed. It thus becomes an undesirable toluene diisocyanate contaminant which often exerts an adverse effect when the diisocyanate is used in the production of polyurethane foam. Therefore, in order to avoid this contamination problem, it is necessary to remove the by-product impurity from the toluene diamine before the latter is used in making toluene diisocyanate. Such removal is achieved by a special distillation operation which is an expensive step that adds to the cost of toluene diamine manufacture.

To eliminate the formation of N-alkyl toluene diamine, it has been proposed to carry out the hydrogenation reaction in the absence of aliphatic alcohol solvent. However, such an expedient has the added effect of reducing the hydrogenation reaction rate or adversely affecting the efficiency of that reaction. Thus from a practical or economic standpoint, it does not provide a satisfactory solution to the problem.

Now an improvement has been found in the abovedescribed hydrogenation process for substantially eliminating the formation of N-alkyl toluene diamine. This objective is achieved, according to the invention, by carrying out the hydrogenation reaction in the presence of a relatively small proportion of carbon monoxide. Thus the invention provides a simple and relatively inexpensive solution to the problem without otherwise adversely affecting the rate or efficiency of the hydrogenation reaction.

The improvement disclosed herein applies to any process wherein a dinitrotoluene is hydrogenated, in the presence of an aliphatic alcohol, to the corresponding toluene diamine and wherein N-alkyl toluene diamine is formed as a by-product. Thus the dinitrotoluene can be any isomer of this compound or a mixture of isomers. Illustrative are the 2,3-, 2,4-, 2,5-, 2,6-, 3,4-and 3,5-isomers and mixtures thereof. However, it is preferred to employ a non-vicinal isomer or mixtures of such isomers such as 2,4-, 2,5-, 2,6-, and 3,5-dinitrotoluene. The most preferred dinitrotoluene isomers are 2,4-dinitrotoluene, 2,6-dinitrotoluene and mixtures thereof.

In carrying out the hydrogenation reaction, any aliphatic alcohol may be employed that serves as a reaction solvent medium without adversely interfering with the hydrogenation reaction or the product thereof. Usually the unsubstituted alkyl monoalcohols are employed which contain from 1 to 8, and preferably 1–4, carbon atoms. Illustrative are methanol, ethyl alcohol, isopropyl alcohol, butyl alcohol, pentyl alcohol, and mixtures thereof. The most preferred alcohol solvent is methanol.

Widely varying amounts of the alcohol solvent may be used in carrying out the hydrogenation reaction. Thus any suitable proportion of alcohol may be employed such as from about 25 to about 2,000, and preferably about 100–1,000, parts per every 100 parts by weight of the dinitrotoluene.

The hydrogenation reaction is preferably carried out in the presence of a hydrogenation catalyst. Any of the variety of catalysts which have been disclosed in the prior art for promoting this type of a reaction may be employed. It is generally preferred to employ metallic catalysts including mixtures comprising such catalysts. These catalysts may be pelleted, granular or powdered, although the powdered form is preferred, such as having a particle size from about 2 to about 400 microns. Furthermore, the catalysts may be either supported on a carrier or unsupported. Some of the useful metallic catalysts which may be employed together with references to their preparation are provided in U.S. Pat. No. 3,232,989 which issued Feb. 1, 1966 to D. E. Graham et al. The entire disclosure of this patent is incorporated herein by reference. A particularly preferred group of catalysts is comprised of nickel, platinum, palladium and mixtures thereof; and in accordance with the most preferred embodiment of the invention, a catalyst comprised of Raney nickel is employed.

The proportion of hydrogenation catalyst may be varied over a wide range. Thus any suitable proportion which is effective in catalyzing the hydrogenation reaction may be employed. Usually a catalytic proportion is employed such as from about 0.1 to about 25 percent, and preferably about 0.3–20 percent, by weight of the dinitrotoluene.

In accordance with the invention, the hydrogenation of dinitrotoluene is carried out in the presence of carbon monoxide gas. This gas may be fed into the reaction zone as a separate stream or as component of the hydrogen stream. The latter practice is preferred, the carbon monoxide being spiked into the hydrogen stream before this is introduced into the reaction zone.

Following the teachings of the invention, it is significant to note that the carbon monoxide is used in a relatively small proportion, so that the formation of toluene diamine is effected primarily via the hydrogenreduction of dinitrotoluene. This is important for two reasons. One is that using relatively large proportions of carbon monoxide results in contamination of the hydrogenation catalyst, thereby reducing its effectiveness. Secondly, hydrogen is generally more effective than carbon monoxide in bringing about the amination of dinitrotoluene.

The proportion of carbon monoxide which is used according to the invention may be varied, generally speaking, from about 0.05 to about 20 percent by volume based on the volume of hydrogen that is employed. However, pursuant to the preferred embodiments of the invention, a carbon monoxide proportion is used which varies from about 0.1 to about 10, and still more preferably about 0.3–6, percent by volume based on the volume of hydrogen.

Following prior art practice, in carrying out the hydrogenation of dinitrotoluene, usually a sufficient proportion or pressure of hydrogen is used to provide approximately at least the stoichiometric amount which is required to reduce the dinitrotoluene to the corresponding toluene diamine. Preferably such a proportion is used as to saturate the reactor contents with hydrogen. For example in practice a reactor to which the dinitrotoluene, solvent and catalyst have been added, is supplied with hydrogen at a pressure from about 25 to about 2,000 psig and preferably about 100–1,000 psig. The hydrogenation reaction is carried out at any suitable temperature. Usually elevated temperatures are employed such as from about 50° to about 200°, and preferably about 90°–150°C.

Any suitable procedure may be employed in practicing the process of the invention. For example a mixture of dinitrotoluene, aliphatic alcohol solvent and catalyst is first fed to a reactor which is equpped with a mechanical agitator and a thermometer. Conventional means is provided for controlling the temperature inside the reactor. Hydrogen and carbon monoxide, which are supplied in separate streams or as a single stream, are then fed to the reactor preferably via one or more inlets located below the surface of the dinitrotoluene-solvent mixture, the hydrogen pressure being regulated to the desired level. The agitated mixture is heated to the desired temperature and maintained at that temperature until the reaction is completed. A liquid reaction product mixture, consisting mainly of toluene diamine, alcohol solvent, water and catalyst, is thus obtained. The toluene diamine is then recovered from this mixture by filtering off the catalyst and distilling off the alcohol solvent. In accordance with one embodiment of the invention, the process described herein may be carried out on a continuous basis following for example the procedure of U.S. Pat. No. 3,356,728 which issued to J. J. Cimerol et al on Dec. 5, 1967. The entire disclosure of this patent is incorporated herein by reference.

The improved hydrogenation process of the invention provides a relatively simple and economical method for preparing toluene diamine which is substantially free of N-alkyl toluene diamine impurity. Furthermore, this result is achieved without otherwise hindering the hydrogenation reaction or adversely affecting product yield. Thus obtained the toluene diamine can be used, directly and without further purification, in the preparation of toluene diisocyanate following prior art phosgenation techniques. The toluene diisocyanate can in turn be used to advantage in the preparation of polyurethane elastomers and forms.

The following examples are provided to illustrate the invention. In these examples, all parts and percentages are by weight unless otherwise specified.

EXAMPLE 1

A 300 mls. autoclave, which was equipped with a thermometer and a mechanical agitator, was purged first with nitrogen and then with hydrogen. It was then charged with 45 grams of 2,4-dinitrotoluene, 84 grams of methanol, and 6.8 grams of Raney nickel catalyst. The continuously stirred mixture was heated to 120°C, and hydrogen gas, which was spiked with carbon monoxide, was introduced into the autoclave through a dip tube discharging below the surface of the mixture. The proportion of carbon monoxide in the hydrogen feed was one percent by volume. A sufficient volume of the carbon monoxidespiked hydrogen was supplied to provide a pressure within the autoclave of 400 psig. The hydrogenation reaction was allowed to proceed to completion over a period of 12 minutes. During that period, the stirred autoclave was maintained at 120°C. Thereafter, the feed of hydrogen was discontinued and the autoclave was opened and allowed to cool to room temperature. The reaction product mixture was then filtered to remove the nickel catalyst. Liquid and gas phase chromatographic analysis revealed the composition of the filtrate to be as follows:

| | | |
|---|---|---|
| 2,4-toluene diamine | : | 18.2% |
| 2,4-dinitrotoluene | : | none |
| methanol | : | 55.8% |
| N-methyl toluene diamine | : | none |
| Water | : | 16.0% |

COMPARISON 1

Essentially the same procedure of Example 1 was followed except that instead of the carbon monoxide-spiked hydrogen, pure hydrogen was used. A liquid phase chromatographic analysis of the filtered reaction product mixture revealed the presence of 1900 ppm. of N-methyl toluene diamine by-product.

COMPARISON 2

This comparison demonstrates the need for using an alcohol solvent in order to achieve an adequate rate of reaction. The general procedure of Comparison 1 was followed using 149 grams of 2,4-dinitrotoluene, 7.9 grams of Raney nickel catalyst, but no methanol solvent. Although the product of the reaction was found to contain no N-methyl toluene diamine, the reaction itself was time-consuming. Thus it was completed only after 185 minutes reaction time as compared with the reaction of Example 1 which was complete in 12 minutes.

What is claimed is:

1. In a process for preparing toluene diamine which comprises reacting dinitrotoluene with hydrogen in the presence of an aliphatic alcohol solvent and a hydrogenation catalyst comprised of nickel, platinum or palladium, the improvement which comprises carrying out said reaction in the presence of a proportion of carbon monoxide ranging from about 0.1 to about 10 percent by volume based on the volume of hydrogen which is used.

2. The process of claim 1 wherein said catalyst is comprised of Raney nickel and said solvent is methanol.

3. The process of claim 1 wherein said alcohol is an unsubstituted alkyl monoalcohol having 1–8 carbon atoms.

4. The process of claim 3 wherein said proportion of carbon monoxide ranges from about 0.3 to about 6.0 percent by volume based on the volume of said hydrogen.

5. The process of claim 4 wherein said dinitrotoluene is employed in the form of a non-vicinal isomer or a mixture of nonvincinal isomers.

6. The process of claim 5 wherein said catalyst is comprised of Raney nickel.

7. The process of claim 6 wherein said alcohol has 1–4 carbon atoms.--

8. The process of claim 7 wherein said dinitrotoluene is 2,4-dinitrotoluene, 2,6-dinitrotoluene or a mixture thereof.

9. The process of claim 8 wherein a reaction temperature of about 90°-150°C is employed.--

10. The process of claim 9 wherein said solvent is methanol.

11. The process of claim 10 wherein said carbon monoxide is combined with said hydrogen before the latter is reacted with said dinitrotoluene.

12. The process of claim 11 wherein said hydrogen is supplied at a pressure of about 100–1,000 psig.

13. The process of claim 12 wherein said methanol is employed in a proportion of about 100–1,000 parts per every 100 parts by weight of said dinitrotoluene.

* * * * *